United States Patent
Chen

(10) Patent No.: US 8,454,670 B2
(45) Date of Patent: Jun. 4, 2013

(54) LIGHT THERAPY DEVICE

(75) Inventor: Ga-Lane Chen, Santa Clara, CA (US)

(73) Assignee: Hon Hai Precision Industry Co., Ltd., New Taipei (TW)

( * ) Notice: Subject to any disclaimer, the term of this patent is extended or adjusted under 35 U.S.C. 154(b) by 157 days.

(21) Appl. No.: 13/108,994

(22) Filed: May 17, 2011

(65) Prior Publication Data

US 2012/0215290 A1    Aug. 23, 2012

(30) Foreign Application Priority Data

Feb. 18, 2011    (TW) .............................. 100105510 A

(51) Int. Cl.
*A61N 5/06*    (2006.01)

(52) U.S. Cl.
USPC .......................................................... 607/88

(58) Field of Classification Search
USPC ...................... 607/88–94; 128/898
See application file for complete search history.

(56) References Cited

U.S. PATENT DOCUMENTS

| | | | |
|---|---|---|---|
| 6,888,779 B2 * | 5/2005 | Mollicone et al. | 368/10 |
| 8,092,381 B2 * | 1/2012 | Edwards | 600/300 |
| 2005/0015122 A1 * | 1/2005 | Mott et al. | 607/88 |
| 2010/0130833 A1 * | 5/2010 | Mott et al. | 600/300 |
| 2010/0179469 A1 * | 7/2010 | Hammond et al. | 604/20 |
| 2011/0137217 A1 * | 6/2011 | Shinnick | 601/89 |

* cited by examiner

*Primary Examiner* — Henry M Johnson, III
(74) *Attorney, Agent, or Firm* — Altis Law Group, Inc.

(57) ABSTRACT

A light therapy device includes a number of light emitting elements, a detection module, a determination module, and a control module. The detection module is configured to detect a body parameter of a human body. The determination module is in communication with the detection module and configured to receive the body parameter and output a fatigue level corresponding to the body parameter. The control module is in communication with the determination module and the light emitting elements. The control module is configured to receive the fatigue level and control the light emitting elements to emit lights with an irradiation intensity for a preset period of time in response to receiving the fatigue level. The irradiation intensity and the preset period of time have a predetermined relationship with the fatigue level.

11 Claims, 2 Drawing Sheets

LIGHT THERAPY DEVICE

BACKGROUND

1. Technical Field

The present disclosure relates to therapy devices, and particularly, to a light therapy device.

2. Description of Related Art

The circadian rhythm or the related physiological rhythm of the human beings or animals is closely related to the natural lighting rhythm. Yet, the circadian rhythm of human beings adapts to the changes of the natural lighting rhythm slowly. For example, as a traveler travels to different time zones, the human body of the traveler cannot adjust the internal clocks easily, thus results in jet lag. Jet lag effects working efficiency and results in rhythm disorder of sleep.

However, results show that radiation with special lighting can efficiently help the rhythm disorder of sleep. Therefore, a known light therapy machine is employed to help a person who has rhythm disorder of sleep. The light therapy machine adjusts the lighting rhythm of the human body according a manually operation, and then changes the circadian rhythm of the human body, thereby reaching a therapeutic purpose. Nevertheless, the manually operation is basically depended on a diagnosed result from a special doctor, and the known light therapy machine needs manual operation, that is time consuming and it is easy make mistakes.

Therefore, it is desirable to provide a light therapy device which can overcome the problems described above.

DETAILED DESCRIPTION

Exemplary embodiments of the disclosure will now be described in detail, with reference to the accompanying drawing.

Figure 1:
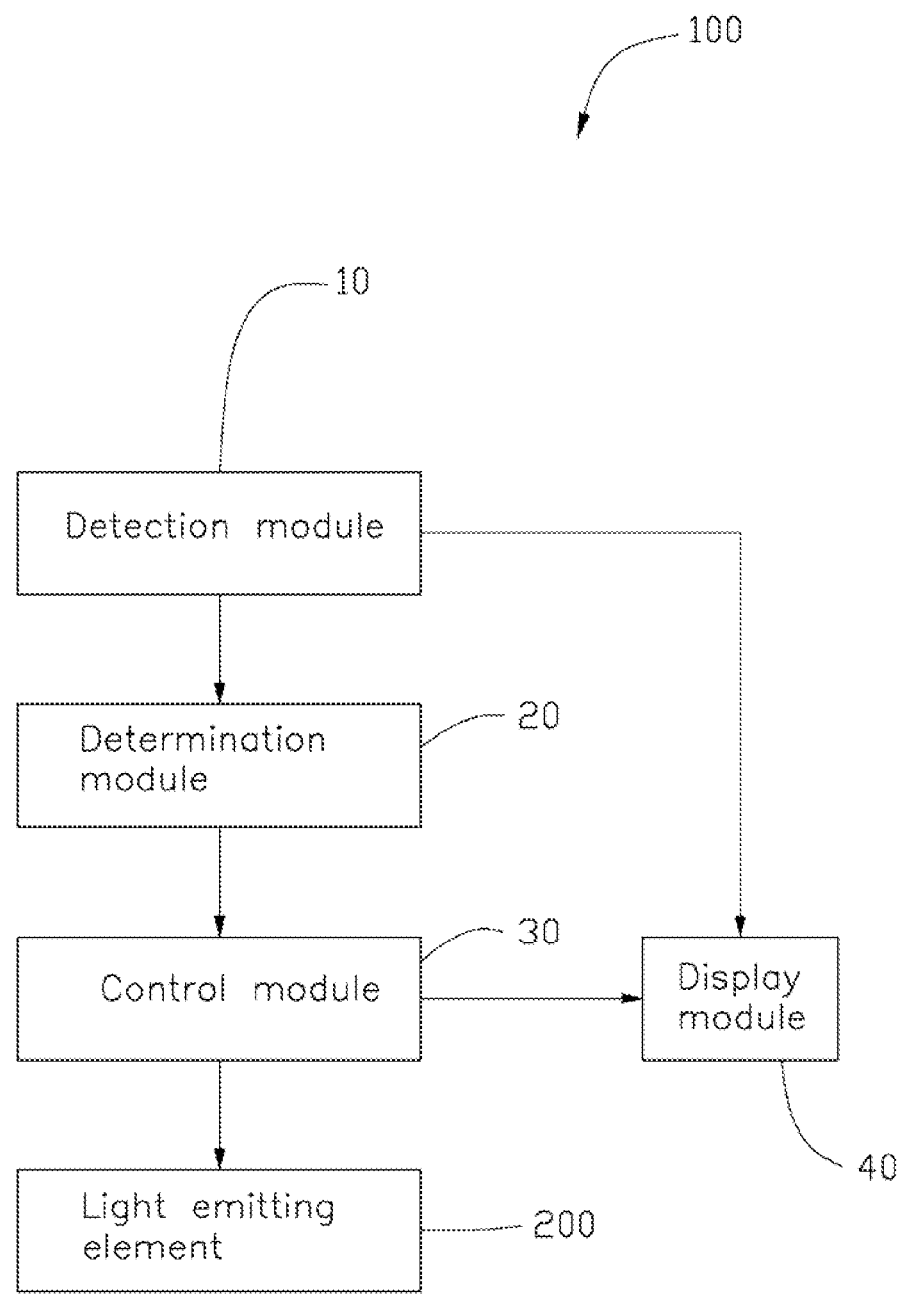
FIG. 1 is a functional block diagram of a light therapy device, according to an exemplary embodiment.

FIG. 1 is a functional block diagram of a light therapy device 100, according to an exemplary embodiment. The light therapy device 100 includes a detection module 10, a determination module 20, a control module 30, and a number of light emitting elements 200. In the present embodiment, the light therapy device 100 is configured to help a person who has jet lag.

The light emitting elements 200 emit lights according to the output signals from the control module 30. In this embodiment, the light emitting element is Organic Light Emitting Diode (OLED). The light emitting elements 200 can radiate different sections of the human body, e.g. eyes, knees, and/or the back. In this embodiment, the different sections of the human body are defined at the knees and the back. In particular, the light therapy device 100 has a chair shape or a belt shape. A user can sit on the light therapy device 100 or be surrounded by the light therapy device 100 during therapy.

The detection module 10 is configured to detect a body parameter N of a human body before light therapy. In this embodiment, the body parameter N can be a rhythm of a heartbeat, reflex, blood pressure, grip strength, or urine protein. In the present embodiment, the body parameter N is the heartbeat.

The determination module 20 is configured to receive the body parameter N and output a fatigue level T corresponding to the body parameter N. The fatigue level T can indicate an activity gradient or fatigue gradient of the human body. In this embodiment, the determination module 20 presets a first spreadsheet with the relationship between the body parameter N and the fatigue level T. For example, the fatigue level T is chosen from level 1, level 2, and level 3, depending on the body parameter N. In the present embodiment, when the body parameter N is between 60 beats per minute and 100 beats per minute, the fatigue level T will be confirmed to be level 1, which shows the rhythm of heartbeat is in an acceptable range and the human body is in a desirable state. When the body parameter N is less than 60 beats per minute, the fatigue level T will be confirmed to be level 2, which shows the human body is in a tired state. When the body parameter N is greater than 100 beats per minute, the fatigue level T will be confirmed to be level 3, which shows the human body is in an excited state.

In a different embodiment, however, the number of levels of fatigue level T, the way of scaling the range of the body parameter N in each level, as well as the corresponding values of the fatigue level T can be varied or adjusted due to the electrical characteristics and the design of the different processor used in the embodiment.

The control module 30 is configured to signal the light emitting elements 200 to emit lights with a corresponding irradiation intensity and irradiation time, according to the current fatigue level T determined by the determination module 20. In detail, the control module 30 prestores a second spreadsheet with values of the irradiation intensity and the irradiation time, in accordance with the fatigue level T. For example, when the fatigue level T is at level 1, the control module 30 reads the irradiation intensity and the irradiation time both as zero from the second spreadsheet. Then it controls the light emitting elements 200 not to be ignited, since the human body is in a common state and has no need to have light therapy at that time. When the fatigue level T is at level 2, the control module 30 controls the light emitting elements 200 to emit light at a first irradiation intensity and maintain a first irradiation time, to radiate the different sections of the human body. When the fatigue level T is at level 3, the control module 30 controls the light emitting elements 200 to emit light at the second irradiation intensity and maintain a second irradiation time, to radiate the different sections of the human body. In the present embodiment, the first irradiation intensity equals to 2000° K to 3000° K, simulating a color temperature of the sunrise or the sunset, and the second irradiation intensity equals to 5000° K to 6000° K for simulating a color temperature of the noon-light. In addition, the first irradiation time is 15 minutes, while the second irradiation time is 30 minutes.

In the present embodiment, the light therapy device 100 further includes a display module 40 configured to display the body parameter N detected by the detection module 10 and the fatigue level T, the value of the irradiation intensity and the irradiation time corresponding to the fatigue level T.

Figure 2:
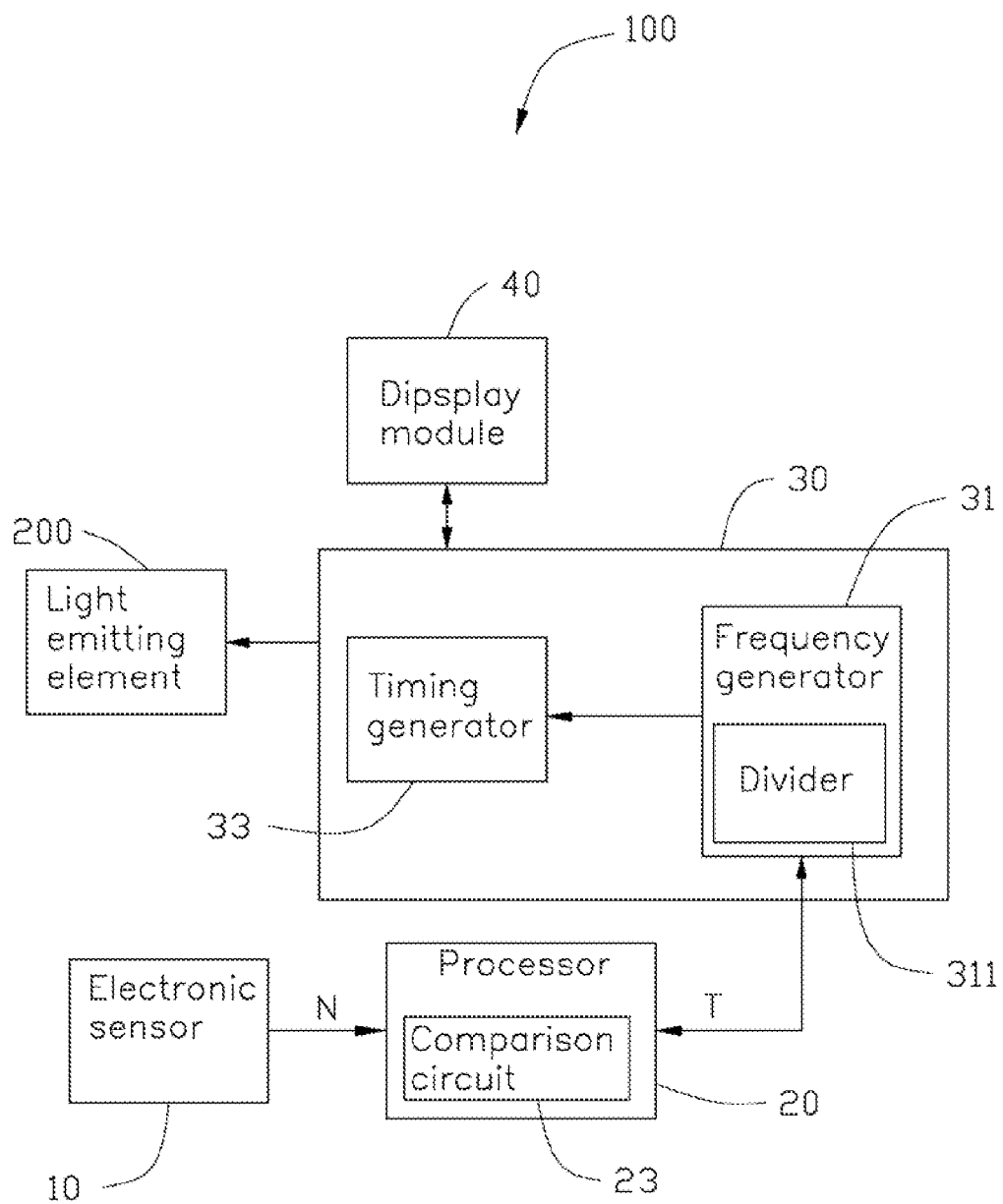
FIG. 2 is a structural diagram of the light therapy device of FIG. 1.

Referring to FIG. 2, in one embodiment, the detection module 10 may be an electronic sensor, the determination module 20 may be a processor. The processor 20 is electrically connected to the electronic sensor 10. The processor 20 receives the body parameter N from the electronic sensor 10 and outputs the fatigue level T according to the body parameter N. In this embodiment, a comparison circuit 23 is built inside the processor 20. The comparison circuit 23 contains the first spreadsheet that describes the corresponding relationship between the body parameter N and the fatigue level T. When the processor 20 receives the body parameter N, the fatigue level T can be obtained from the comparison circuit 23 using method such as data comparison, interpolation. In a different embodiment, the comparison circuit 23 can have a built-in arithmetic unit (not shown). When the body parameter N is sent to the processor 20, this arithmetic unit can obtain the corresponding fatigue level T.

The control module 30 is implemented by a frequency generator 31 and a timing generator 33 in the present embodiment.

The frequency generator 31 is electrically connected to the processor 20, in which the frequency generator 31 receives the fatigue level T from the processor 20, and outputs an oscillatory frequency F according to the fatigue level T. The oscillatory frequency F can generate the light emitting elements 200 to emit light at the first intensity or at the second intensity. In this embodiment, the frequency generator 31 comprises a divider 311 and pre-stores a predetermined frequency F0. The divider 311 performs a division on the predetermined frequency F0 and the received fatigue level T. For instance, the oscillatory frequency F is obtained from dividing the predetermined frequency F0 by the value of the fatigue level T. In one embodiment, when the predetermined frequency F0 is 60 MHz, the corresponding oscillatory frequency F could be 60 MHz, 30 MHz, and 20 MHz, respectively according to 1, 2, and 3 of the levels. In order to keep consistence with the present embodiment, when the fatigue level T is 1, the frequency generator 31 does not generate an oscillatory frequency F and maintains a standby state, until the fatigue level T is changed.

In a different embodiment, however, the value of the predetermined frequency F0 can be adjusted in order to accommodate to the different designs in the frequency generator 31. Furthermore, in another embodiment, the divider 311 of the frequency generator 31 can be replaced by an arithmetic unit that performs a different mathematical operation. Hence, the oscillatory frequency F can be obtained by performing the mathematical operation on the fatigue level T and the predetermined frequency F0 using the arithmetic unit.

The timing generator 33 is electrically connected to the frequency generator 31, configured for receiving the oscillatory frequency F from the frequency generator 31 and obtaining the irradiation time according to a number of clock impulses based on the oscillatory frequency F. In one embodiment, the irradiation time is reciprocal to the oscillatory frequency F. Since the irradiation time has such a corresponding relationship with the oscillatory frequency F, the irradiation time can be changeable with the oscillatory frequency F.

The light emitting elements 200 are electrically connected to the frequency generator 31 and the timing generator 33, and emit light with the irradiation intensity in the irradiation time, according to the oscillatory frequency F and the clock impulses.

In a different embodiment, however, the control module 30 can further include a voltage adjustable structure (not shown), which is configured to adjust the voltage on the light emitting elements 200 to control the irradiation intensity thereof. In this situation, the frequency generator 31 and the timing generator 33 can cooperatively control the irradiation time.

In summary, when the light therapy device 100 starts to work, the electronic sensor 10 first detects the different sections of the human body and receives the body parameter N. Then the determination module 20 determines the fatigue level T in accordance with the body parameter N in the first spreadsheet. The control module 30 continuously signals the light emitting elements 200 to emit lights according to the predetermined values of the irradiation intensity and irradiation time in the second spreadsheet. As such, the light therapy device 100 can automatically implement the therapy operation to the human body, thus, increasing convenience.

It will be understood that particular exemplary embodiments are shown and described by way of illustration only. The principles and the features of the present disclosure may be employed in various and numerous exemplary embodiments thereof without departing from the scope of the disclosure. The above-described exemplary embodiments illustrate the scope of the disclosure but do not restrict the scope of the disclosure.

What is claimed is:

1. A light therapy device, comprising:
a plurality of light emitting elements;
memory;
one or more processors;
one or more modules stored in the memory and configured for execution by the one or more processors, the one or more modules comprising:
a detection module configured to detect a body parameter of a human body;
a determination module in communication with the detection module and configured to receive the body parameter and output a fatigue level corresponding to the body parameter; and
a control module in communication with the determination module and the light emitting elements, the control module being configured to receive the fatigue level and control the light emitting elements to emit lights with an irradiation intensity for a preset period of time in response to receiving the fatigue level, the irradiation intensity and the preset period of time having a predetermined relationship with the fatigue level;
wherein the body parameter is the rhythm of heartbeat, when the body parameter is between 60 beats per minute and 100 beats per minute, the fatigue level is confirmed to be level 1; when the body parameter is less than 60 beats per minute, the fatigue level is confirmed to be level 2; when the body parameter is greater than 100 beats per minute, the fatigue level is confirmed to be level 3.

2. The light therapy device of claim 1, further comprising a display module configured to display the body parameter, the fatigue level, the value of the irradiation intensity, and the preset period of time.

3. The light therapy device of claim 1, wherein the determination module presets a first spreadsheet with a relationship between the body parameter and the fatigue level.

4. The light therapy device of claim 1, wherein the control module is configured to control the light emitting elements not to be ignited on a condition that the fatigue level is at level 1; the control module is configured to control the light emitting elements to emit lights with a first irradiation intensity for a first preset period of time on a condition that the fatigue level is at level 2; the control module is configured to control the light emitting elements to emit lights with a second irradiation intensity for a second preset period of time on a condition that the fatigue level is at level 3.

5. The light therapy device of claim 4, wherein the first irradiation intensity is in a range from 2000° K to 3000° K, simulating a color temperature of the sunrise or the sunset, and the second irradiation intensity is in a range from 5000° K to 6000° K, simulating a color temperature of the noonlight.

6. The light therapy device of claim 1, wherein the control module prestores a second spreadsheet with a relationship between the irradiation intensity, the preset period of time, and the fatigue level.

7. The light therapy device of claim 1, wherein the light emitting elements are organic light emitting diodes.

8. The light therapy device of claim 1, wherein the detection module is an electronic sensor, the determination module is electrically connected to the electronic sensor, and the determination module is configured to receive the body parameter from the electronic sensor and output the fatigue level.

9. The light therapy device of claim 8, wherein the determination module comprises a comparison circuit configured to obtain the fatigue level on a condition that the processor receives the body parameter.

10. The light therapy device of claim 9, wherein the control module comprises a frequency generator and a timing generator, the frequency generator is electrically connected to the processor, the frequency generator is configured to receive the fatigue level from the processor and output an oscillatory frequency according to the fatigue level, the timing generator is electrically connected to the frequency generator and configured to receive the oscillatory frequency from the frequency generator and output the preset period of time based on the oscillatory frequency.

11. The light therapy device of claim 10, wherein the frequency generator comprises a divider and pre-stores a predetermined frequency, the divider is configured to perform a division based on the predetermined frequency and the received fatigue level.

* * * * *